(12) United States Patent
Kals et al.

(10) Patent No.: US 8,428,743 B2
(45) Date of Patent: Apr. 23, 2013

(54) EQUAL LOUDNESS CONTOUR WITH CHANNEL SPECIFIC MAP LAWS

(75) Inventors: Mathias Kals, Innsbruck (AT); Peter Schleich, Telfs (AT); Dirk Meister, Axams (AT)

(73) Assignee: Med-El Elektromedizinische Geraete GmbH, Innsbruck (AT)

( * ) Notice: Subject to any disclaimer, the term of this patent is extended or adjusted under 35 U.S.C. 154(b) by 21 days.

(21) Appl. No.: 13/107,035

(22) Filed: May 13, 2011

(65) Prior Publication Data

US 2011/0264169 A1    Oct. 27, 2011

Related U.S. Application Data

(63) Continuation-in-part of application No. 13/091,357, filed on Apr. 21, 2011, which is a continuation-in-part of application No. 12/910,007, filed on Oct. 22, 2010.

(60) Provisional application No. 61/254,279, filed on Oct. 23, 2009.

(51) Int. Cl.
*A61N 1/00* (2006.01)

(52) U.S. Cl.
USPC ............................................................ 607/57

(58) Field of Classification Search ...................... 607/57
See application file for complete search history.

(56) References Cited

U.S. PATENT DOCUMENTS

2011/0081033 A1* 4/2011 Kitazawa ...................... 381/321

\* cited by examiner

*Primary Examiner* — George Manuel
*Assistant Examiner* — Robert N Wieland
(74) *Attorney, Agent, or Firm* — Sunstein Kann Murphy & Timbers LLP

(57) ABSTRACT

A method is described for generating electrode stimulation signals for an implanted electrode array. An acoustic audio signal is processed to generate band pass signals each representing an associated band of audio frequencies. Stimulation information is extracted from the band pass signals to generate stimulation event signals defining electrode stimulation signals. The stimulation event signals are mapped according to independent channel-specific loudness functions to produce a set of electrode stimulation signals within channel-specific minimum and maximum threshold levels. The electrode stimulation signals are developed into a set of output electrode pulses to the electrodes in the implanted electrode array.

18 Claims, 8 Drawing Sheets

Equal-loudness contours from ISO 226:2003 revision
Original ISO standard shown for 40-phons

EQUAL LOUDNESS CONTOUR WITH CHANNEL SPECIFIC MAP LAWS

This application is a continuation-in-part of co-pending U.S. patent application Ser. No. 13/091,357, filed Apr. 21, 2011, which is a continuation-in-part of co-pending U.S. patent application Ser. No. 12/910,007, filed Oct. 22, 2010, which claims priority from U.S. Provisional Patent Application 61/254,279, filed Oct. 23, 2009, all of which are incorporated herein by reference.

FIELD OF THE INVENTION

The present invention relates to cochlear implants, and specifically to the signal processing used therein.

BACKGROUND ART

FIG. 1 shows major functional blocks in the signal processing arrangement typical of existing cochlear implant (CI) systems wherein band pass signals containing stimulation timing and amplitude information are assigned to stimulation electrodes. Preprocessor Filter Bank 101 pre-processes an initial acoustic audio signal, e.g., automatic gain control, noise reduction, etc. Each band pass filter in the Preprocessor Filter Bank 101 is associated with a specific band of audio frequencies so that the acoustic audio signal is filtered into some N band pass signals, $B_1$ to $B_N$ where each signal corresponds to the band of frequencies for one of the band pass filters.

The band pass signals $B_1$ to $B_N$ are input to a Stimulation Pulse Generator 102 which extracts signal specific stimulation information—e.g., envelope information, phase information, timing of requested stimulation events, etc.—into a set of N stimulation event signals $S_1$ to $S_N$, which represent electrode specific requested stimulation events. For example, channel specific sampling sequences (CSSS) may be used as described in U.S. Pat. No. 6,594,525, which is incorporated herein by reference.

Pulse Mapping Module 103 applies a non-linear mapping function (typically logarithmic) to the amplitude of the each band-pass envelope. This mapping function typically is adapted to the needs of the individual CI user during fitting of the implant in order to achieve natural loudness growth. This may be in the specific form of functions that are applied to each requested stimulation event signal $S_1$ to $S_N$ that reflect patient-specific perceptual characteristics to produce a set of electrode stimulation signals $A_1$ to $A_N$ that provide an optimal electric representation of the acoustic signal.

The Pulse Mapping Module 103 controls loudness mapping functions. The amplitudes of the electrical pulses are derived from the envelopes of the assigned band pass filter outputs. As shown in FIG. 2, a logarithmic function with a form-factor C typically may be applied to stimulation event signals $S_1$ to $S_N$ as a loudness mapping function, which generally is identical across all the band pass analysis channels. In different systems, different specific loudness mapping functions other than a logarithmic function may be used, though still just one identical function is applied to all channels as shown in FIG. 2 to produce the electrode stimulation signals $A_1$ to $A_N$ outputs from the Pulse Mapping Module 103.

Finally, patient specific stimulation is achieved by individual amplitude mapping and pulse shape definition in Pulse Shaper 104 which develops the set of electrode stimulation signals $A_1$ to $A_N$ into a set of output electrode pulses $E_1$ to $E_N$ to the electrodes in the implanted electrode array which stimulate the adjacent nerve tissue.

Looking more closely at the operation of the Pre-Processor Filter Bank 101, CI signal processing seeks to imitate the natural behavior of a normal ear. A pre emphasis filter typically is used to reflect ISO loudness contours (ISO 226) of normal hearing (NH) subjects. For example, a pre emphasis filter can be implemented using a high pass filter with a cut off frequency of 1200 Hz and an attenuation of 6 dB per octave, reducing signal amplitudes by about 18 dB for frequencies around 150 Hz. Since the pre emphasis filter is located before or is integrated within the channel specific band filters of the Pre-Processor Filter Bank 101, signal components are attenuated into a lower usable dynamic range in all the succeeding signal processing stages, resulting in a lower accuracy of the stimulation amplitude. FIG. 9 illustrates this loss of accuracy showing a logarithmic mapping using representative values of c=512, MCL=0.8 and THR=0.08. The dotted line in FIG. 9 shows the maximum upper input and output limit for a 150 Hz sinusoid attenuated by a pre emphasis filter. In this case, the maximum possible input signal $ENV_{norm}$ is 0.126 and the maximum possible output signal $ENV_{log}$ is 0.563. Signal $ENV_{norm}$ and $ENV_{log}$ correspond to normalised signal $S_n$ and $E_n$ of FIG. 1, respectively (n={1, ..., N}). In the upper x-axis the corresponding sound pressure level in dB is shown (with no AGC).

Another disadvantage of using a high pass pre emphasis filter in the Pre-Processor Filter Bank 101 is that the sound level dependency of the ISO loudness contour will not be considered. For example, as shown in FIG. 10, an 89.5 phon contour is much shallower than a 35.5 phon contour and this cannot be modeled by high pass filtering (where the marks T and M also show minimum and maximum threshold levels for a 150 Hz sinusoid).

The Pulse Mapping Module 103 maps the stimulation event signal (typically signal envelope amplitudes) using a logarithmic map law function. This compensates for the exponential loudness growth of electrical stimulation. Since signal processing channels with low frequencies (e.g., <1200 Hz) are attenuated by the pre emphasis filter, the map law input signal cannot reach maximum amplitude, and in these attenuated channels consequently the most comfortable loudness (MCL) level also cannot be reached in the output electrode pulses. FIG. 9 shows this effect for a 150 Hz sinusoid, which corresponds to a low frequency band where the center frequency covers typical male and female $F_0$. The attenuation before map law results in an unwanted reduction of the dynamic range of the corresponding signal and possibly in decreased hearing performance for CI listeners. Moreover, the resulting electric stimuli do not match to ISO loudness contours of NH subjects since only frequency-dependent and no amplitude-dependent attenuation is used.

As described above, the ISO loudness contours are roughly approximated by a high pass filter (pre emphasis filter). Instead of this high pass filter, a weighting of the channel specific band pass filter coefficients or a channel specific gain can be used. But any of these methods results in a reduction of the usable dynamic range (DR) in the succeeding signal processing stages. For example, after envelope extraction, amplitudes can be mapped by using:

$$ENV_{log} = \frac{\log(1 + c \cdot ENV_{norm})}{\log(1 + c)} \cdot (MCL - THR) + THR \quad \text{(Equ. 1)}$$

where $ENV_{norm}$ represents the normalized envelope amplitude relative to the maximum possible envelope amplitude as obtained from the signal processing (proportional to sound pressure level of the input signal), and c represents the logarithmic mapping parameter. Minimum (THR) and a maximum (MCL) levels are the electrode-specific current levels. In FIG. 9, one specific example of the logarithmic mapping using Equation 1 is given where a 150 Hz sinusoid is used which corresponds to a high male fundamental frequency $F_0$. Due to the pre emphasis filter, this signal can reach a maximum value of $ENV_{log}=0.563$ after mapping (indicated by the dotted line in FIG. 9). In this case, assuming MCL=0.8 and THR=0.08, the DR is $20*\log_{10}(0.563/0.08)=17$ dB. Without a pre-emphasis filter the DR would be $20*\log_{10}(0.8/0.08)=20$ dB. Thus the DR effectively is reduced by approximately 3 dB when a pre emphasis filter is used prior to the map-law stage.

SUMMARY OF THE INVENTION

Embodiments of the present invention are directed to methods, systems and software code for generating electrode stimulation signals for an implanted electrode array. An acoustic audio signal is processed to generate band pass signals each representing an associated band of audio frequencies. Stimulation information is extracted from the band pass signals to generate stimulation event signals defining electrode stimulation signals. The stimulation event signals are mapped according to independent channel-specific loudness functions (e.g., logarithmic functions) to produce a set of electrode stimulation signals within channel-specific minimum and maximum threshold levels. The electrode stimulation signals are developed into a set of output electrode pulses to the electrodes in the implanted electrode array.

Embodiments of the present invention also include methods, systems and software code for generating electrode stimulation signals for an implanted electrode array. An acoustic audio signal is processed to generate band pass signals each representing an associated band of audio frequencies and scaled to reflect independent channel specific loudness functions (e.g., logarithmic functions and/or frequency-related functions). These independent functions ensure an optimal loudness growth in electrical stimulation for each electrode contact. Besides a logarithmic mapping, these functions can also incorporate different electrode specific properties, e.g. neuronal survival or electrode location. Stimulation information is extracted from the band pass signals to generate stimulation event signals defining electrode stimulation signals. The stimulation event signals are mapped according to a common loudness scaling parameter adapted to cooperate with the loudness functions to produce a set of electrode stimulation signals within channel-specific minimum and maximum threshold levels. The electrode stimulation signals are developed into a set of output electrode pulses to the electrodes in the implanted electrode array.

Stimulation event signals below the minimum threshold level may be mapped to a minimum stimulation event signal, while those above the maximum threshold level may be mapped to a maximum stimulation event signal. The threshold levels may be based on system sound pressure level (SPL) limits. The loudness functions may be based on ISO normal hearing contours.

DETAILED DESCRIPTION OF SPECIFIC EMBODIMENTS

Figure 4:
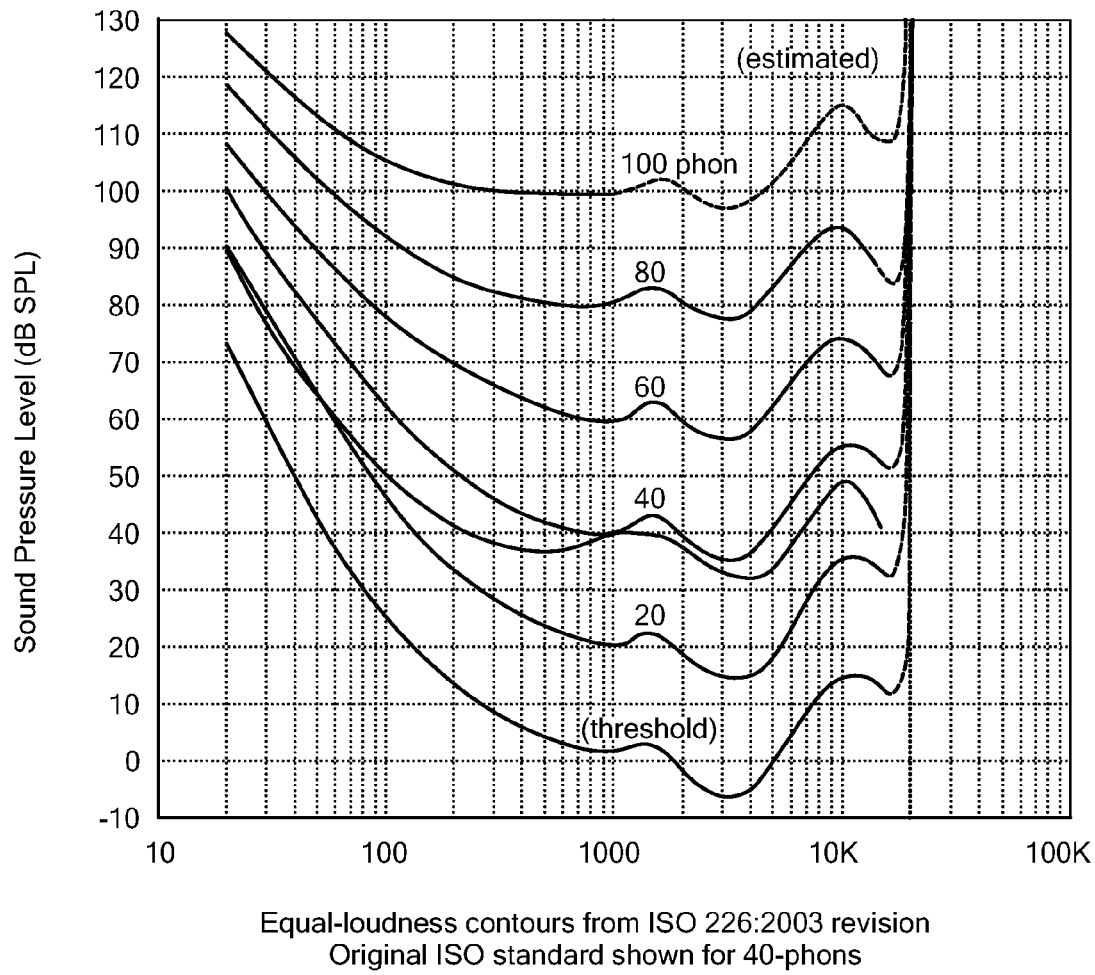
FIG. 4 shows various equal-loudness contours according to ISO 226:2003 for a normal hearing person.

Existing CI systems do not take into account psychoacoustical properties of normal hearing such as the equal-loudness contours shown is FIG. 4. In normal hearing subjects, the acoustical level difference in loudness curves between the 20 phon and 100 phon is noticeably different between high frequencies and low frequencies. For normal hearing, loudness grows faster at 80 Hz than at 1000 Hz, so that where the difference in phons at 80 Hz amounts to just 57 $dB_{SPL}$, at 1000 Hz the difference is about 80 $dB_{SPL}$.

This effect has not been accounted for in existing CI systems, and little or no effort has been made to correctly code the acoustic intensity or sound level across frequencies and thereby stimulation sites. Comfortable loudness levels are typically defined based on a post-implantation fitting process that determines a hearing threshold (THR) for the user and a level at which maximum comfortable/acceptable loudness is reached (MCL). MCLs and THRs can vary from channel to channel for a CI user.

During existing post-implant fitting procedures, loudness mapping functions are rarely changed even though beneficial effects on speech understanding and naturalness of perceived sounds could be expected. Hoth S., *Indication For The Need Of Flexible And Frequency Specific Mapping Functions In Cochlear Implant Speech Processors*. Eur. Arch. Otorhinolaryngol 264:129-138 (2007) (incorporated herein by reference) describes a subjective categorical loudness scaling procedure which could be used to determine an optimum frequency specific loudness mapping. Hoth concludes that the loudness mapping function of a CI can be optimized by individually scaling the loudness of electric and acoustic stimuli. The procedure he describes is rather time consuming and is limited to CI systems that do not allow channel specific loudness mapping.

U.S. Patent Publication 20070043403 describes a method of processing sound signals for an auditory prosthesis that uses a model of loudness perception by people with normal hearing. The current level of a first stimulation electrode is determined so that the loudness matches a normal hearing perception model for loudness. The electrode excitation pattern is then recalculated and the steps are repeated for each remaining electrode. Thus amplitude adjustments are individually performed on each electrode based on a loudness perception model using the concept of excitation patterns. This iterative procedure ends with a final excitation pattern that should provide a more natural loudness percept.

Figure 1:
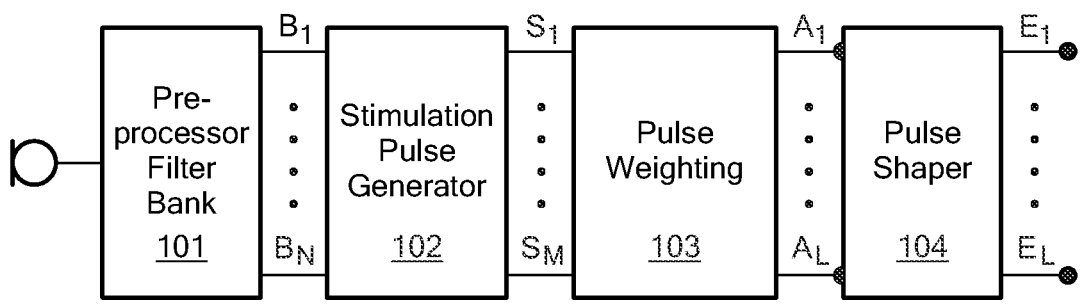
FIG. 1 shows major signal processing blocks of a typical cochlear implant system.
Figure 2:
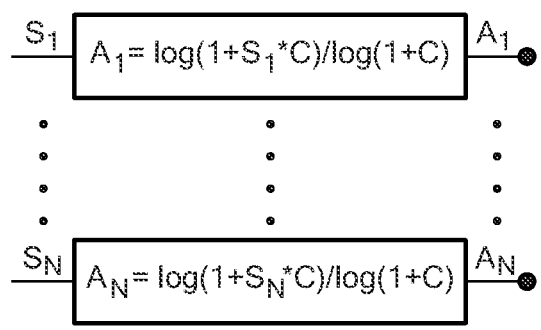
FIG. 2 illustrates typical implementation of channel specific loudness mapping based on a single logarithmic function.
Figure 3:
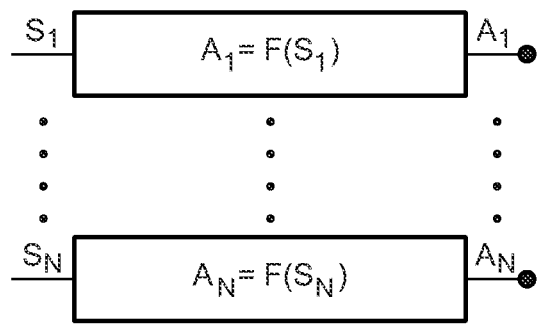
FIG. 3 illustrates the general functional form of channel specific loudness mapping as done in existing cochlear implant systems.
Figure 7:
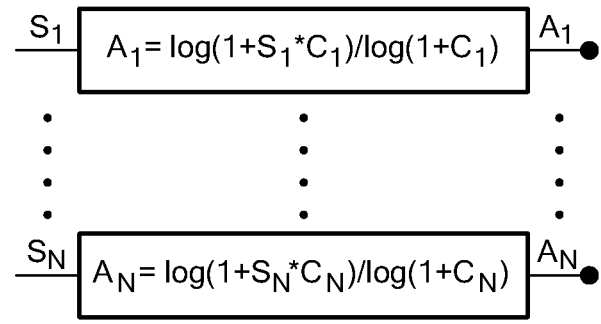
FIG. 7 shows a typical implementation of independent channel specific loudness mapping according to an embodiment of the present invention based on use of a logarithmic function.

Embodiments of the present invention extend the signal processing arrangement for cochlear implants of the Pulse Mapping Module 103 as shown in FIG. 1 to provide channel specific amplitude mapping so that the stimulation event signals $S_1$ to $S_N$ are determined according independent channel-specific loudness functions to produce the electrode stimulation signals $A_1$ to $A_N$. For example, as shown in FIG. 7, the channel specific amplitude mapping can be defined by a logarithmic function with at least one set of parameters ($C_n$, where n={1, . . . , N}) for the individual adjustment of frequency-specific and/or signal-specific loudness growth:

$$A_n = \log(1 + S_n \cdot C_n)/\log(1 + C_n) \quad \text{(Equ. 2)}$$

Parameters of specific loudness functions can be determined, for example, based on a categorical loudness scaling as already used in audiology testing. This results in at least one additional stimulation current contour such as the half-loudness contour HL shown in FIG. 5. The logarithmic functions may specifically reflect ISO normal hearing contours, or a loudness percept determined with respect to a basal-most electrode in the implanted electrode array, or psychoacoustic hearing factors, for example, from a post-implant patient fitting process.

An MCL contour that resembles the loudness percept of normal hearing subjects could be determined by presenting an acoustic stimulus at the most basal electrode at a level that results in stimulation at MCL of that channel, e.g. 90 phon. The most basal electrode transmits the frequencies where normal hearing is less sensitive to sound pressure than for most other frequencies (see FIG. 5), so it is unlikely that an equal-loudness contour with this level will exceed the comfortable level of the other electrodes. The neighboring electrode could be acoustically stimulated with a level that corresponds to the 90 phon ISO loudness contour. The stimulation current could be adjusted until the subject perceives the stimuli with the same loudness as the previous electrode. This procedure would be repeated with every electrode, each time the stimulating current would be adjusted to the neighboring electrode. A second contour could be measured at subjective "half loudness" (HL) relative to the MCL contour.

Figure 5:
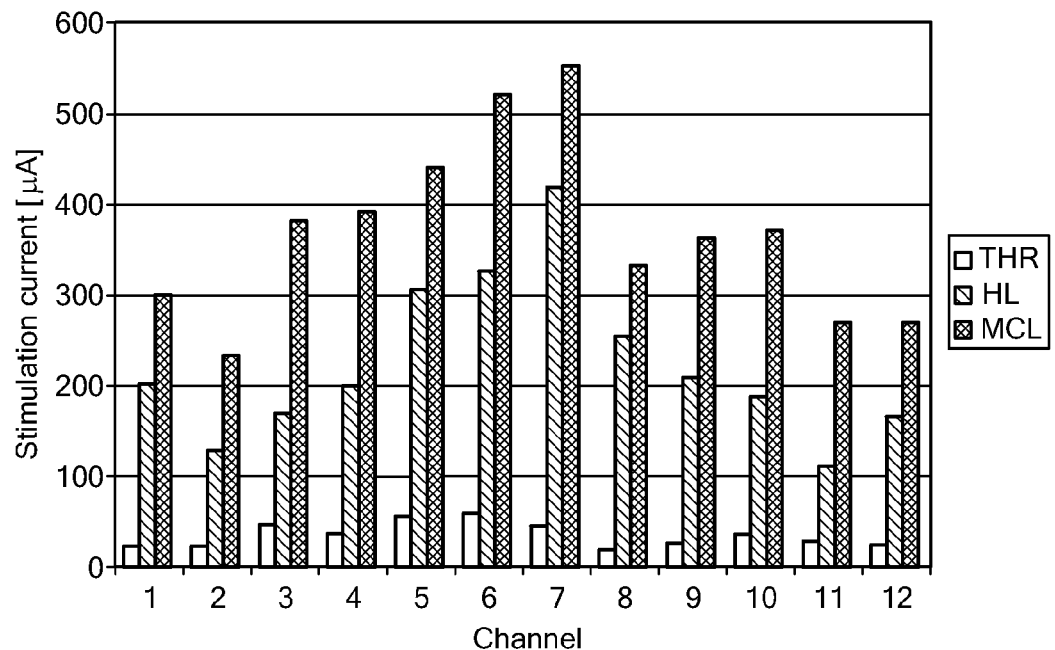
FIG. 5 charts stimulation current at threshold, maximum loudness, and "half loudness."
Figure 6:
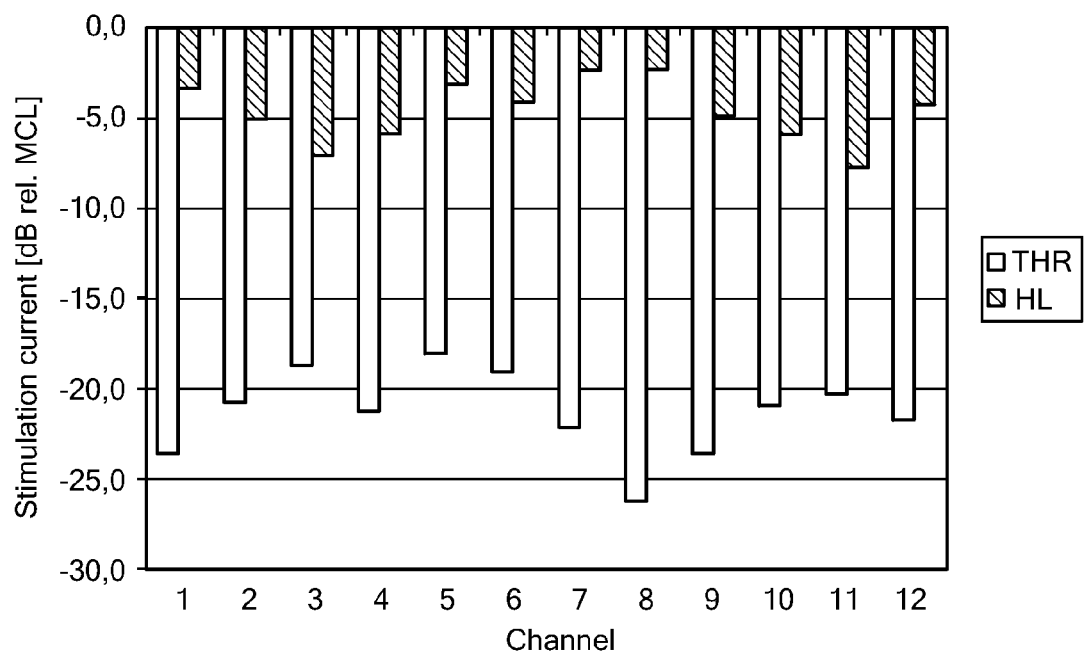
FIG. 6 charts stimulation current at threshold and "half loudness" in dB relative MCL.
Figure 8:
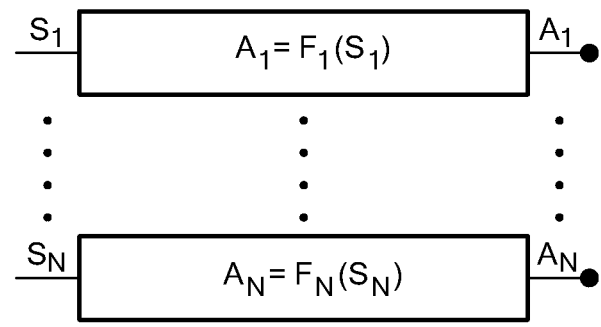
FIG. 8 shows the general functional form of independent channel specific loudness mapping according to an embodiment of the present invention.
Figure 9:
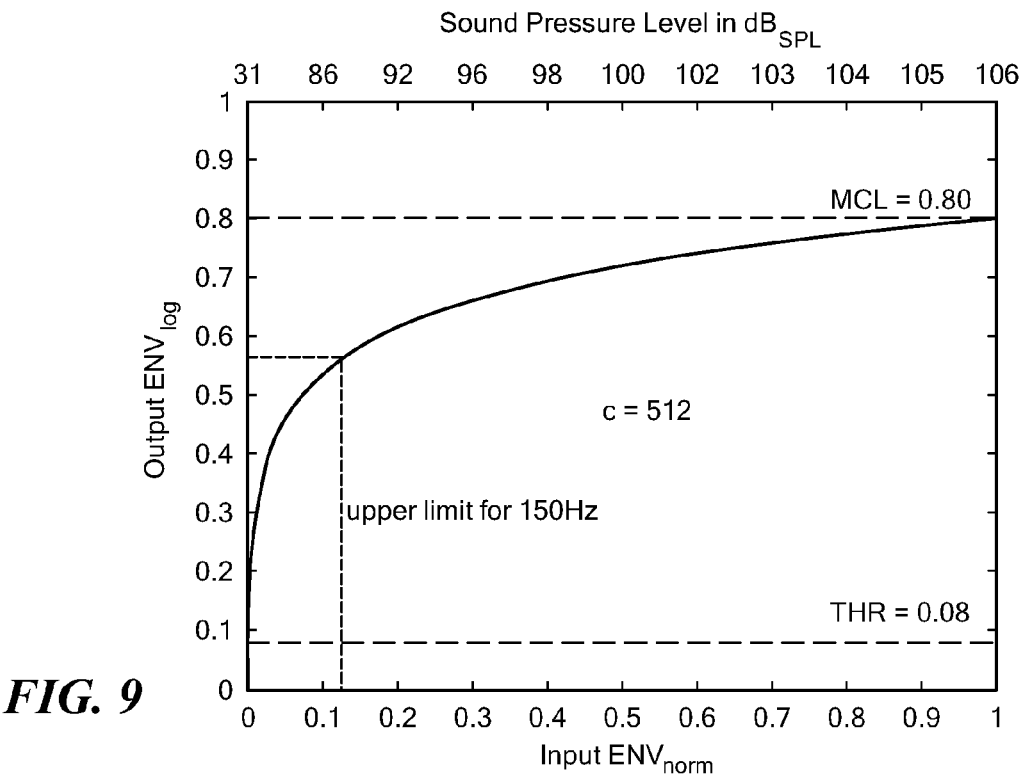
FIG. 9 shows an example of logarithmic mapping of pre-emphasis filter input and output envelope signals.

FIG. 6 compares the THR and HL levels from FIG. 5 in terms of dB relative to MCL. Largely different ratios between THR and HL can be seen (e.g. channels 3 and 8). The values of $C_1$ to $C_N$ could then be calculated from the three contours. Accordingly, alternative loudness mapping functions $F_1$ to $F_N$ besides the specific logarithmic function shown in FIG. 7 could be used to parameterize loudness on different channels, as shown in FIG. 8.

Loudness perception of different acoustic sounds can be adjusted by individually adjusting mapping functions in different frequency bands. Thus loudness can be balanced across channels not only at hearing thresholds THR and maximum comfortable loudness MCL, but also at intermediate sound amplitudes, e.g. at "half loudness" HL. In addition, ISO loudness contours known from normal hearing may be modeled. Losses in speech understanding due to unbalanced stimulation amplitudes also may be resolvable. Fitting of the system can be performed relatively easily, for example, using categorical loudness scaling or loudness balancing at half loudness relative to one channel which is similar to balancing of MCLs. Besides relatively easy fitting arrangements, complex algorithms also are avoided such as those described in application US 2007/0043403 A1.

To perform loudness scaling based on the ISO loudness curve, each frequency band can be treated separately by the Pulse Mapping Module 103. Thus, another embodiment of the present invention is based on selecting the ISO normal hearing curves within the maximum and minimum supported sound pressure levels of a given CI system, and thereby maximizing available dynamic range. Instead of using a pre-emphasis high-pass filter and a single map-law for all channels, channel specific map-laws are used. In these map-laws, the ISO loudness contours of natural hearing subjects are considered within channel-specific minimum and maximum threshold levels T and M that reflect the system sound pressure limits $L_{min}$ and $L_{max}$ and the specific frequency range. Such an arrangement would still be characterized as shown by FIGS. 7 and 8.

Figure 10:
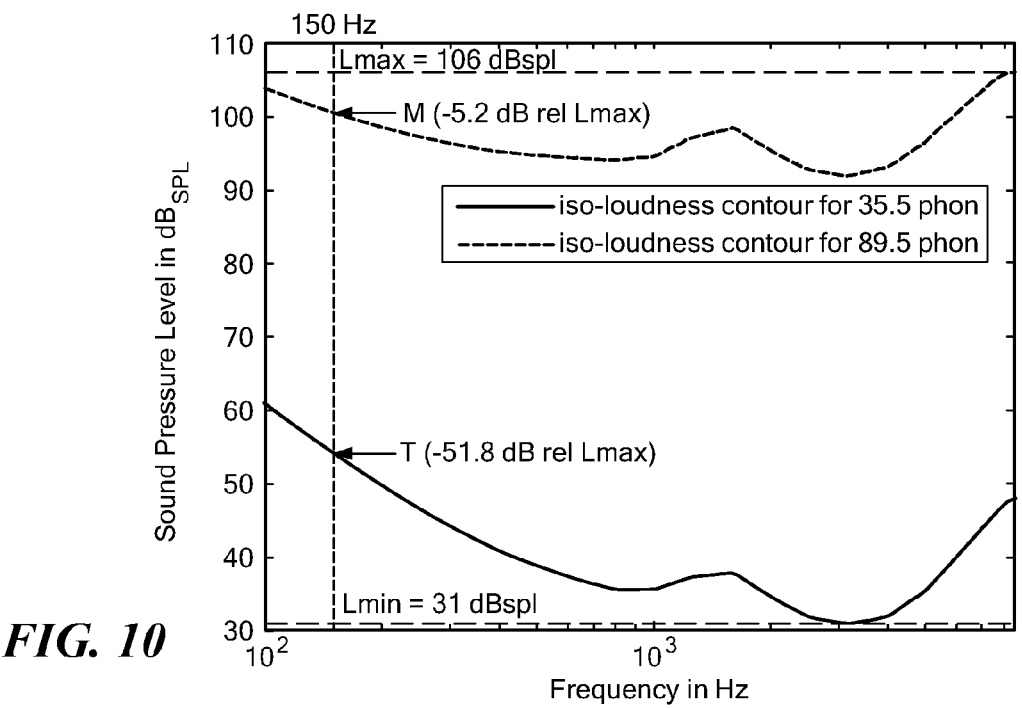
FIG. 10 shows examples of ISO loudness contours for different maximum and minimum sound pressure limits.

For example, FIG. 10 shows examples of ISO loudness contours for different maximum and minimum sound pressure limits in a system with a specific lower limit of $L_{min}$=31 $dB_{SPL}$ and an upper limit of $L_{max}$=106 $dB_{SPL}$ assumed across a frequency range of 100 to 8500 Hz. For determining maximum and minimum possible phon levels (i.e., maximizing dynamic range) ISO loudness curves within the sound-processor frequency range are investigated. For the maximum level, the highest phon level is used were the $L_{max}$=106 $dB_{SPL}$ is not exceeded, while the minimum level is given by lowest phon level which does not fall below $L_{min}$=31 $dB_{SPL}$. Based on these criterions, in this case ISO loudness curves between 35.5 and 89.5 phon are possible and can be shaped just by attenuation of frequency bands. For example, a 150 Hz sinusoid needs to be reduced by 51.8 dB (point T) and 5.2 dB (point M), respectively, relative to $L_{max}$ for 35.5 and 89.5 phon level, respectively. This reduction can be integrated in a modified logarithmic mapping function:

$$ENV_{log} = \begin{cases} THR, & \text{if } ENV_{norm} < T \\ \dfrac{\log\left(1 + c \cdot \dfrac{ENV_{norm} - T}{M - T}\right)}{\log(1 + c)} \cdot & \text{if } T \leq ENV_{norm} \leq M \\ (MCL - THR) + THR, & \\ MCL, & \text{if } ENV_{norm} > M. \end{cases} \quad \text{(Equ. 3)}$$

Figure 11:
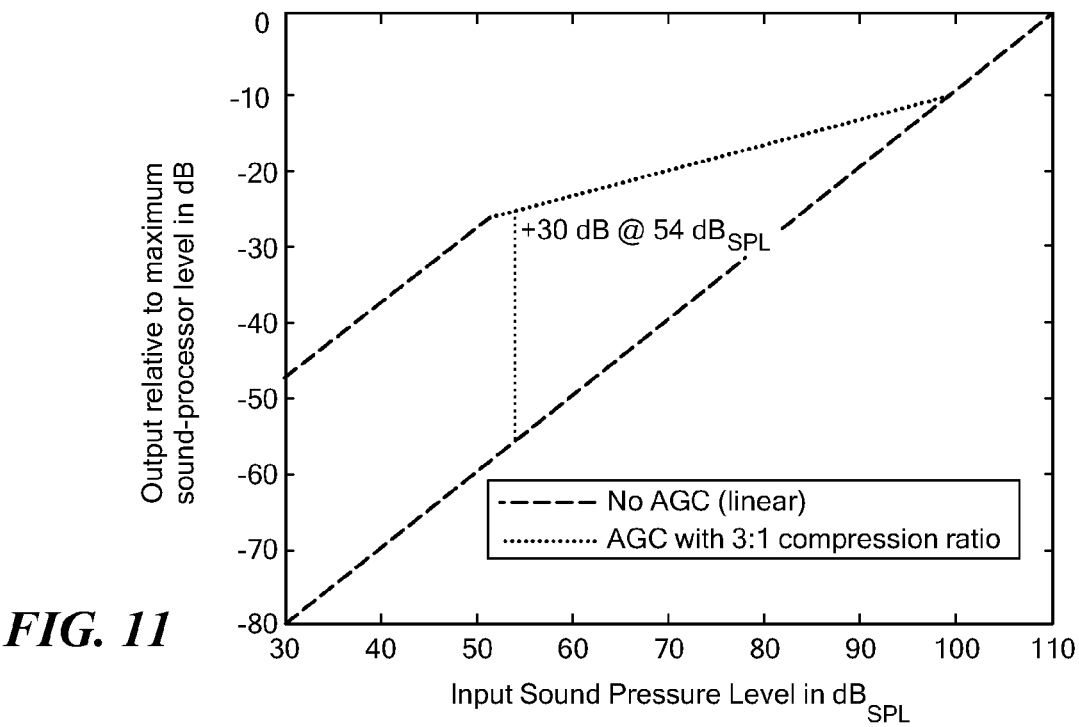
FIG. 11 shows static compression for a typical AGC arrangement.
Figure 12:
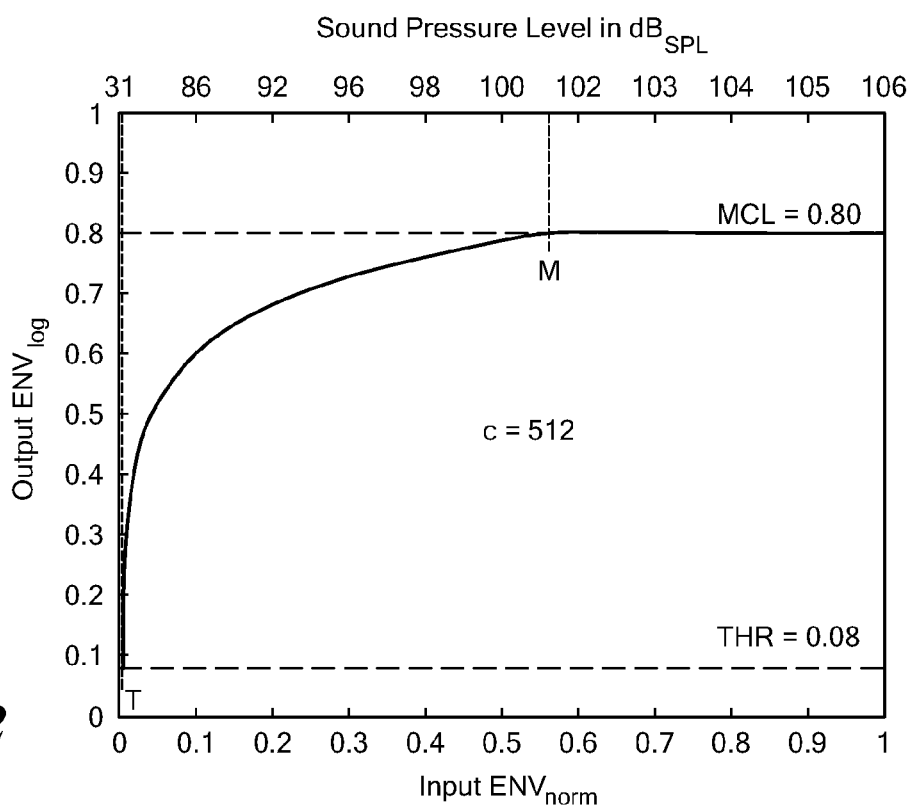
FIG. 12 shows a logarithmic mapping between signal maximum and minimum threshold levels.

Since the input amplitudes are not attenuated in this mapping the full electric dynamic range is utilized in the electrical stimulation as shown in the example of FIG. 12. In systems without automatic gain control (AGC), the minimum threshold T levels are near 0 on linear scale and can be neglected in the mapping. However, in systems with an AGC the stationary amplification typically amplifies low level signals by about 30 dB. FIG. 11 illustrates the static compression effects for a typical AGC arrangement with a 3:1 compression ratio. When the 3:1 static compression ratio is considered in the minimum T and maximum M threshold calculations, this would lead in the 150 Hz sinusoid example to an increase of 30 dB in the T threshold. Consequently, the resulting T threshold would lie around 0.08 (−51.8 dB+30 dB) of the input signal of FIG. 10.

In a practical embodiment, for each channel the band specific T and M thresholds can be calculated from the applicable ISO loudness contours as shown in FIG. 10. With these T and M thresholds, channel-specific logarithmic mapping can performed based on Equation 3. FIG. 12 shows a logarithmic mapping between signal maximum M and minimum T threshold levels where c=512, MCL=0.8, and THR=0.08. T and M thresholds are obtained for a 150 Hz frequency from the ISO loudness contour for 35.5 and 89.5 phon levels. Since the input signal $ENV_{norm}$ is not attenuated by a pre-emphasis filter, the entire electrical dynamic range is accessible. In the upper x axis, the corresponding sound pressure level is shown (no AGC). Here, a channel-specific mapping loudness parameter c, can be utilized as well as a common loudness parameter c for all channels. An individual adjustment of the channel-specific mapping parameter $c_n$ can be performed, for example, by loudness balancing across all channels at a specific phon level (e.g. 65 phon) by adjusting the channel specific loudness parameter $c_n$. This ensures the presence of ISO loudness contours in the entire acoustic loudness range of the sound-processor.

Figure 13:
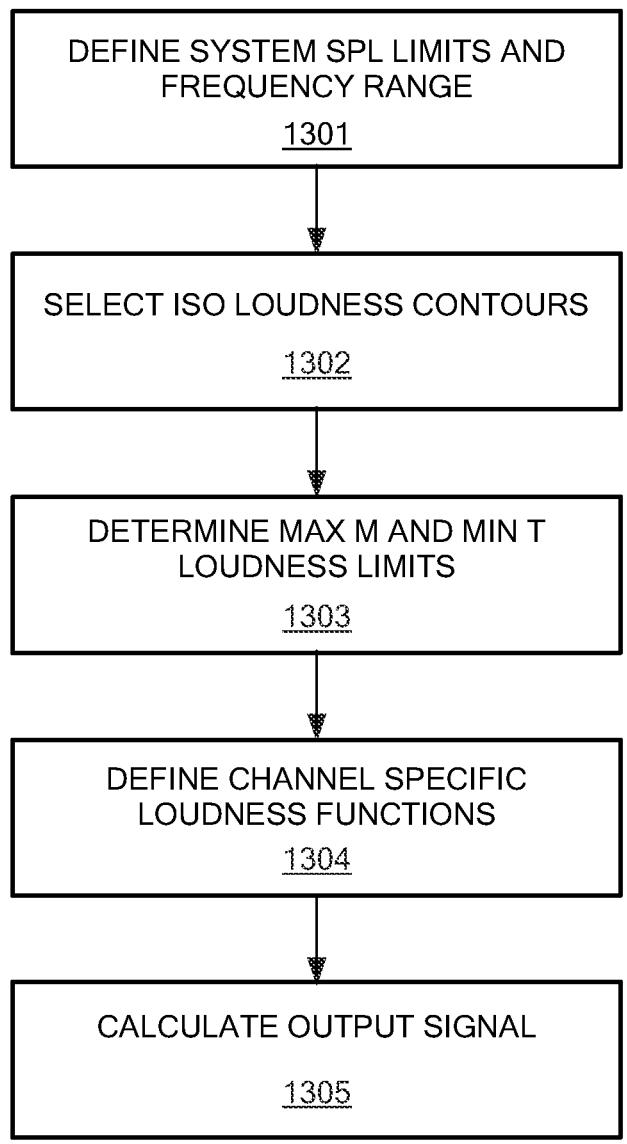
FIG. 13 shows an example of various logical steps in a channel-specific loudness scaling.

FIG. 13 shows an example of the logical steps in such a channel-specific loudness scaling where the scaling stage has an input signal $ENV_{norm}$ and an output signal $ENV_{log}$. Initially the system sound pressure level (SPL) limits $L_{min}$ and $L_{max}$ and frequency range are determined, step 1301. For example, $L_{min}$=31 dB SPL, $L_{max}$=106 dB SPL and f=100–8500 Hz. A set of loudness functions $V_i$—e.g., ISO loudness contours—defined over the selected frequency range are then selected, step 1302. From these, maximum and minimum loudness functions M and T are selected that satisfy one or more performance criterions, step 1303. For example, wherein max(M)=$L_{max}$ and min(T)=$L_{min}$ (see FIG. 10: T is the 35.5 phon curve and M is the 89.5 phon curve). From these, channel-specific loudness functions can be defined, step 1304. That is, for each frequency f within the selected frequency range, values ≤T are mapped to THR (the electrode minimum stimulation level, $ENV_{log}$=THR) and values ≥M are mapped to MCL (the electric maximum comfortable loudness level, $ENV_{log}$=MCL), and values between those two levels are mapped to the channel-specific loudness function (e.g. as shown in Equation 3). The output signal $ENV_{log}$ can then be calculated according to the mapped functions, step 1305.

In comparison to the traditional pre-emphasis and logarithmic mapping approach, this method allows use of ISO loudness contours as in natural hearing subjects. Furthermore, the complete electric dynamic range of each electrode is used accordingly.

Based on the channel-specific mapping with T and M thresholds, the channel-specific mapping parameter $c_i$ can be determined by balancing channels at a specific phone level (e.g. 65 phon) for equal loudness by adjusting $c_n$. If a common mapping loudness parameter c is used for all channels, then no additional effort is needed in contrast to a traditional fitting procedure. Since the required T and M threshold parameters for the channel-specific mapping can be calculated for each channel directly from the iso-loudness contours. Instead of a logarithmic mapping function any other appropriate function can be used in the channel-specific mapping.

Instead of scaling each channel by individual loudness parameters $c_n$, another embodiment could use a common loudness parameter c (that is, one or more general functions common to all channels) but initially "prepare" each envelope channel at the output of the band pass filters so that after scaling it with the common loudness parameter c, the desired output envelope is generated (e.g., again according to the ISO loudness contours). The result would be the same as in the previously described embodiment, but the step for preparing the envelopes occurs at a different point in the signal processing compared to the loudness scaling and it can be separated from this scaling.

Thus more specifically, an embodiment of the present invention also includes an arrangement for generating electrode stimulation signals for an implanted electrode array where an acoustic audio signal is processed to generate band pass signals that each represent an associated band of audio frequencies and that are scaled to reflect independent channel specific loudness functions (e.g., logarithmic functions). Stimulation information is then extracted from the band pass signals to generate stimulation event signals defining electrode stimulation signals. The stimulation event signals are mapped according to a common loudness scaling parameter adapted to cooperate with the loudness functions to produce a set of electrode stimulation signals within channel-specific minimum and maximum threshold levels. The electrode stimulation signals are developed into a set of output electrode pulses to the electrodes in the implanted electrode array.

For example, instead of using a pre emphasis high pass filter with a single map-law for all channels or channel specific map-laws as described earlier, a nonlinear frequency- or channel dependent ISO-loudness contour may be used to map prior single or channel specific map-laws. In this nonlinear frequency dependent mapping, the ISO-loudness contours of normal hearing subjects are considered by introducing frequency dependent threshold levels T(f) and M(f).

Based on the sound pressure limits $L_{MIN}$ and $L_{MAX}$ of a CI-system (lower and upper clipping value) and the frequency range used, the corresponding applicable ISO-loudness contours are selected. For example, in FIG. 10 a system with a lower limit of $L_{MIN}$=31 $dB_{SPL}$ and an upper limit of $L_{MAX}$=106 $dB_{SPL}$ is assumed across a frequency range of 100 to 8500 Hz. For determining maximum and minimum possible phon levels, ISO-loudness curves within the sound-processor frequency range are investigated. For the maximum level, the highest phone level is used were the $L_{MAX}$=106 $dB_{SPL}$ are not exceeded. In contrast, the minimum level is given by lowest phone level which does not fall below $L_{MIN}$=31 $dB_{SPL}$. Based on these criterions in this case curves within 35.5 and 89.5 phon are possible. For example, a 150 Hz sinusoid needs to be reduced by 51.8 dB T(150 Hz) and 5.2 dB M(150 Hz), respectively, relative to $L_{MAX}$ for 35.5 and 89.5 phon level, respectively.

Nonlinear mapping can be performed from the frequency dependent threshold levels T(f) and M(f) nonlinear mapping can be performed by calculating:

$$ENV_{norm,dB} = \begin{cases} L_{MIN}, & \text{if } ENV_{norm,dB} \leq T(f) \\ (L_{MAX} - L_{MIN}) \cdot \\ \left( \dfrac{ENV_{norm,dB} - T(f)}{M(f) - T(f)} - 1 \right), & \text{if } T(f) < ENV_{norm,dB} < M(f) \\ L_{MAX}, & \text{if } ENV_{norm,dB} \geq M(f) \end{cases} \quad \text{(Equ. 4)}$$

where $L_{MIN}$, $L_{MAX}$, T(f), M(f) and $ENV_{norm,dB}$ values are represented in dB. This ensures the presence of ISO-loudness contours in the entire acoustic loudness range of the sound-processor.

Figure 14:
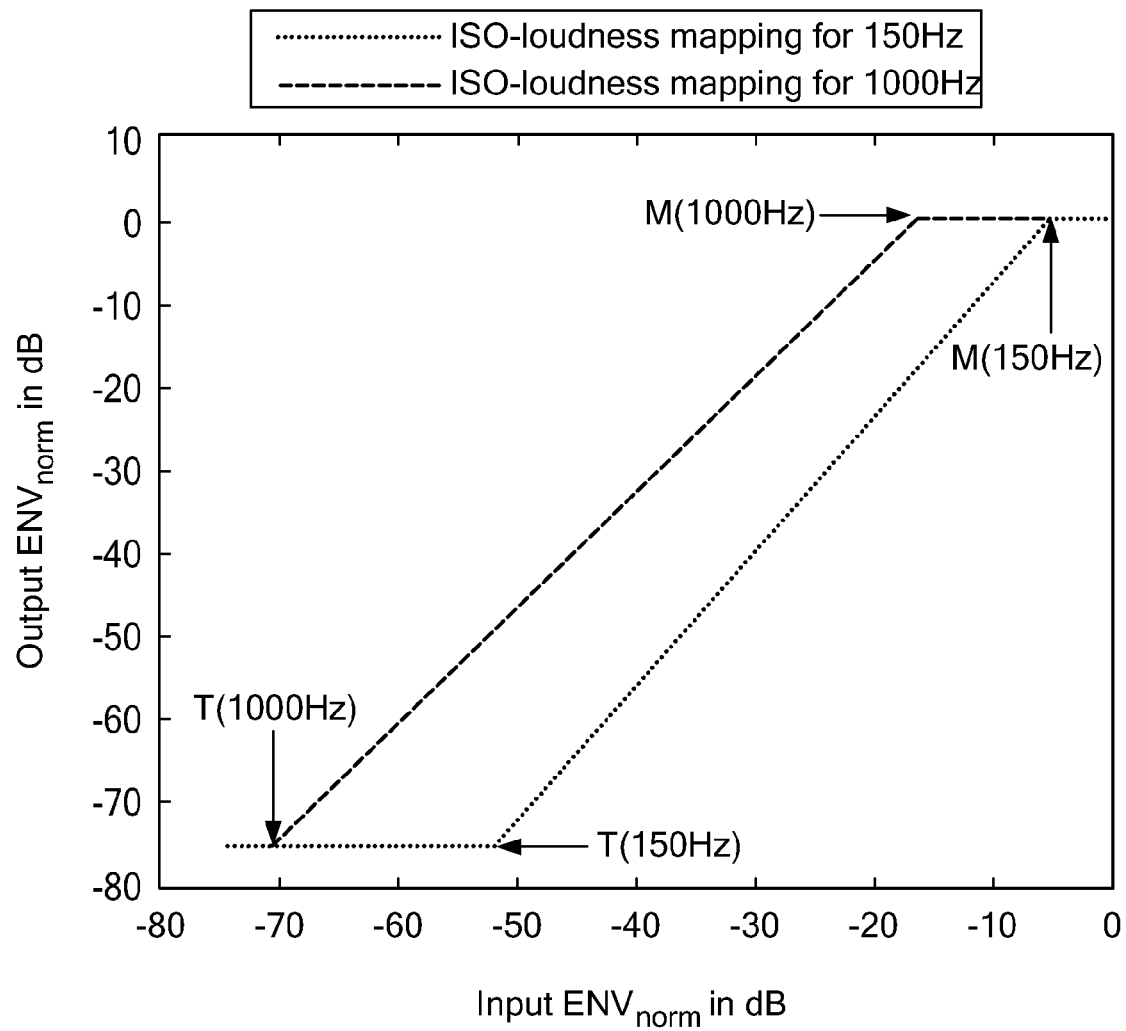
FIG. 14 is shows data for a frequency dependent nonlinear mapping based on ISO loudness contours.

FIG. 14 shows an exemplary illustration of a frequency dependent nonlinear mapping based on ISO-loudness contours for two frequencies, 150 Hz and 1000 Hz. T(f)- and M(f)-thresholds are obtained from 35.5 and 89.5 phon curves and a system with 75 dB dynamic range is assumed. Input levels below T(f) and upper M(f) are mapped to the lower and upper system limit, respectively. After nonlinear mapping a map-law (single or channel specific) stage follows.

In comparison to the traditional pre emphasis filtering this nonlinear channel or frequency-specific mapping with T(f)- and M(f)-thresholds allows ISO-loudness contours as in normal hearing subjects. No channel specific mapping stage is required to reach ISO-loudness contours in CI-systems.

In a system with Fast Fourier Transform (FFT) implementation a frequency dependent mapping can be performed, since frequencies are related to FFT bins. Channel specific nonlinear mapping can be used in band filter based systems. Within each band filter (channel n) a representative frequency $f_n$ is used for the nonlinear mapping, e.g. band center frequency. The channel specific mapping thresholds can be defined by $T_n=T(f_n)$ and $M_n=M(f_n)$.

In contrast to traditional pre emphasis filtering in this method the complete electric dynamic range of each electrode is utilised, when acoustic input signals are within the specified acoustic dynamic range of the CI-System. A system with adaptive or dynamic mapping thresholds would be also feasible, e.g. for considering temporal and spectral masking effects across and within channels.

Embodiments of the invention may be implemented in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of generating electrode stimulation signals for an implanted electrode array, the method comprising:
   processing an acoustic audio signal to generate a plurality of band pass signals each representing an associated band of audio frequencies;
   extracting stimulation information from the band pass signals to generate a set of stimulation event signals defining electrode stimulation signals;
   mapping the stimulation event signals according to independent channel-specific loudness functions based on ISO normal hearing contours to produce a set of electrode stimulation signals within channel-specific minimum and maximum threshold levels; and
   developing the electrode stimulation signals into a set of output electrode pulses to the electrodes in the implanted electrode array.

2. A method according to claim 1, wherein stimulation event signals below the minimum threshold level are mapped to a minimum stimulation event signal.

3. A method according to claim 1, wherein stimulation event signals above the maximum threshold level are mapped to a maximum stimulation event signal.

4. A method according to claim 1, wherein the threshold levels are based on system sound pressure level (SPL) limits.

5. A method according to claim 1, wherein the loudness functions are logarithmic functions.

6. A method according to claim 1, wherein the loudness functions are frequency related.

7. A computer program product implemented in a computer readable storage medium for generating electrode stimulation signals for a plurality of stimulation electrodes in an implanted electrode array, the product comprising:
   program code for processing an acoustic audio signal to generate a plurality of band pass signals each representing an associated band of audio frequencies;
   program code for extracting stimulation information from the band pass signals to generate a set of stimulation event signals defining electrode stimulation signals;
   program code for mapping the stimulation event signals according to independent channel-specific loudness functions based on ISO normal hearing contours to produce a set of electrode stimulation signals within channel-specific minimum and maximum threshold levels; and
   program code for developing the electrode stimulation signals into a set of output electrode pulses to the electrodes in the implanted electrode array.

8. A product according to claim 7, wherein stimulation event signals below the minimum threshold level are mapped to a minimum stimulation event signal.

9. A product according to claim 7, wherein stimulation event signals above the maximum threshold level are mapped to a maximum stimulation event signal.

10. A product according to claim 7, wherein the threshold levels are based on system sound pressure level (SPL) limits.

11. A product according to claim 7, wherein the loudness functions are logarithmic functions.

12. A product according to claim 7, wherein the loudness functions are frequency related.

13. A system for generating electrode stimulation signals for an implanted electrode array, the system comprising:
   means for processing an acoustic audio signal to generate a plurality of band pass signals each representing an associated band of audio frequencies;

means for extracting stimulation information from the band pass signals to generate a set of stimulation event signals defining electrode stimulation signals;

means for mapping the stimulation event signals according to independent channel-specific loudness functions based on ISO normal hearing contours to produce a set of electrode stimulation signals within channel-specific minimum and maximum threshold levels; and means for developing the electrode stimulation signals into a set of output electrode pulses to the electrodes in the implanted electrode array.

14. A system according to claim 13, wherein stimulation event signals below the minimum threshold level are mapped to a minimum stimulation event signal.

15. A system according to claim 13, wherein stimulation event signals above the maximum threshold level are mapped to a maximum stimulation event signal.

16. A system according to claim 13, wherein the threshold levels are based on system sound pressure level (SPL) limits.

17. A system according to claim 13, wherein the loudness functions are logarithmic functions.

18. A system according to claim 13, wherein the loudness functions are frequency related.

\* \* \* \* \*